United States Patent [19]

Welbourn et al.

[11] Patent Number: 4,663,522

[45] Date of Patent: May 5, 1987

[54] INTEGRATING SPHERE DEVICE FOR MEASURING TRANSMISSION OF LIGHT IN OBJECTS

[75] Inventors: Christopher M. Welbourn; Martin P. Smith, both of Maidenhead, England

[73] Assignee: Spandrel Establishment, Vaduz, Liechtenstein

[21] Appl. No.: 784,622

[22] Filed: Oct. 4, 1985

[30] Foreign Application Priority Data

Oct. 5, 1984 [GB] United Kingdom ............ 8425273

[51] Int. Cl.⁴ .................................. H01J 40/14
[52] U.S. Cl. .......................... 250/223 R; 250/228; 356/236; 356/338; 209/576
[58] Field of Search ............ 250/223 R, 216, 221, 250/222.1, 222.2, 224, 226, 228, 229, 231 R, 572, 578; 356/30, 236, 237, 239, 379, 337–343, 73; 209/576–582, 585–588

[56] References Cited

U.S. PATENT DOCUMENTS 3,795,310 3/1974 Buchot et al. ............ 209/778 X
3,826,364 7/1974 Bonner et al. ............ 209/579 X
4,280,625 7/1981 Grobbelaar et al. ............ 209/582

Primary Examiner—Eugene R. LaRoche
Assistant Examiner—David Mis
Attorney, Agent, or Firm—Kerkam, Stowell, Kondracki & Clarke

[57] ABSTRACT

The apparatus measures the transmission of light in successive falling objects. A beam is projected, wide enough to bathe all the facing surface of the object. An integrating sphere is on the other side of the object and its inlet and outlet apertures provide cut-offs so that only a hollow cone of flux scattered from the object is trapped in the integrating sphere, this flux being measured by a detector. The detector is connected to a micro-processor whose output is a measure of the clarity of the object. When the object is not in the beam, the beam falls on a detector so that the reduction in flux sensed by the detector is a measure of the projected area of the object. The micro-processor divides the signal from the detector by the reduction in flux, thereby making the output substantially independent of the size of the object.

32 Claims, 5 Drawing Figures

INTEGRATING SPHERE DEVICE FOR MEASURING TRANSMISSION OF LIGHT IN OBJECTS

BACKGROUND OF THE INVENTION

The present invention relates to apparatus for producing a signal responsive to the transmission of objects, and to a method of determining the light transmission in each of a succession of objects. The objects can be of any suitable type, without limitation, for instance substantially transparent foodstuffs such as sweets, or glass or plastics material articles—the objects can be natural or synthetic.

For instance, sweets could have unwanted inclusions such as bubbles or pieces of opaque foreign matter, or non-homogeneous colourant.

The quality of substantially transparent objects may be affected, usually detrimentally, by the presence of light-absorbing or light-scattering impurities or defects which generally reduce the light transmission in the object.

In general terms, it is desirable to provide means for quantitatively assessing the light transmission in objects, and it is also desirable that the assessment be performed rapidly so that the objects can be sorted automatically into categories according to their light transmissivity or transparency.

THE PRESENT INVENTION

Using the invention, the object is placed in or passed through one or more beams of illuminating radiation and using first responsive means a measurement is made of the intensity of radiation scattered in a forward direction into one or more conceptual hollow cones of appropriate angles. Account is taken of the size of the object by using second responsive means to measure the attenuation of the intensity of the beam or beams, assuming that the object falls within the cross-sectional area of the beam or beams. It will be understood that the term "measurement" does not require absolute measurement, providing some signal is given representative of the value.

Although it is known that the transparency of parallel-sided objects may be assessed by measuring the intensity of light transmitted through them, the present invention enables the light transmissivity or clarity of irregularly-shaped or more generally non-parallel-sided objects to be assessed by measuring the forward scattering into a hollow cone.

PREFERRED EMBODIMENTS

The invention will be further described, by way of example, with reference to the accompanying drawings, in which.

FIGS. 1 TO 4

Three axes 1, 2, 3 represent the respective paths of three different illuminating beams, these paths being mutually orthogonal. A fourth axis 4 represents the path of successive objects through the apparatus, down which the object can fall freely or be projected.

Figure 4:
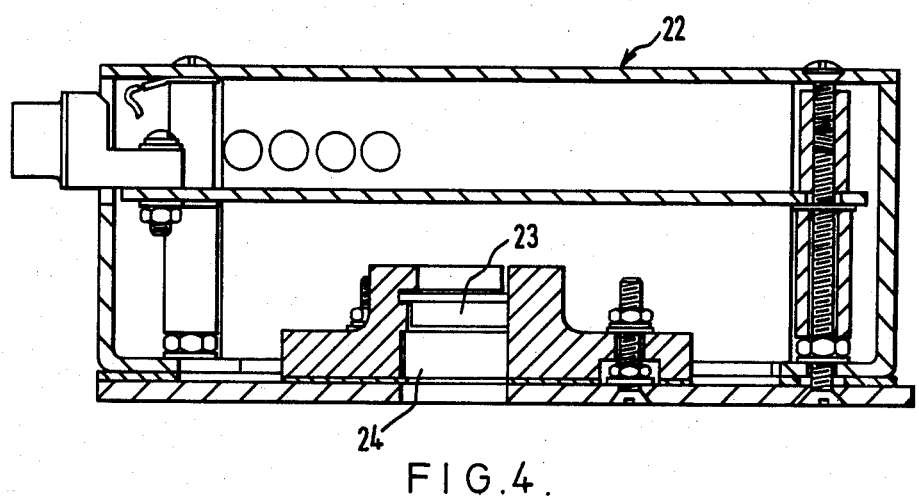
FIG. 4 is a section through the detector unit along the plane II—II indicated in FIG. 1, on a larger scale.

One of the light paths will now be described with reference to FIG. 2. There is a conventional bulb 5 having a rectangular filament, a condenser lens 6, an iris diaphragm 7 to provide coarse adjustment of the beam flux, a first filter 8, a square aperture 9, a lens 10, a second filter 11, a mirror 12 having a known kinematic steering system 13 for pivoting it about an axis normal to the drawing, a lens 14, an iris diaphragm 15 to provide fine adjustment of the beam flux, a position 16 where the light transmission in the object is determined, an integrating cavity 17 generally in the form of a sphere, a mirror 18 having a known kinematic steering system 19 for pivoting it about an axis normal to the drawing, an iris diaphragm 20, a lens 21 and a detector unit 22 which acts as said second responsive means and may have for instance (and as shown in FIG. 4) a large area silicon photo-diode 23 provided with a filter 24. Cooling of the lamp 5 and adjacent parts is provided by a fan (not shown) housed in a housing 25 (see FIG. 1).

The integrating cavity 17 also contains suitable baffles 26 and, shielded by a baffle 26, a small emitter 27 which fires every so often to check that the particular channel is operative within the limits set. A second emitter 28 is provided within the field of view of the detector unit 22 for a similar purpose.

The integrating cavity 17 has circular inlet and outlet apertures 29, 30. The inlet aperture 29 acts to cut off any light scattered from position 16 which is outside a certain conical surface, and the aperture 30 acts to allow any light within a certain conical surface to pass out of the integrating cavity 17. In this way, all light transmitted through the object in a notional hollow cone coaxial with the beam with its apex at position 16 remains within the integrating cavity 17. The cone outer surface will have a half-angle substantially less than 90°, preferably from 30° to 60°, a suitable angle being 37.5°. The inner surface of the cone has a narrow half-angle, preferably from 5° to 10°, a suitable angle being 8.5°. In order to detect the total flux captured by the integrating cavity 17, the integrating cavity 17 has a further aperture 31 associated with another detector unit 32 which in association with the cavity 17 acts as first responsive means for producing a first signal responsive to the total flux of radiation transmitted through the object. The detector unit 32 can also have a large area silicon photodiode and be similar to the unit 22, but may have a different electronic gain to that of the detector unit 22. The integrating cavity 17 also has a drain opening 33 for discharging any object which may pass into the integrating cavity 17 by mistake.

The optical arrangement may be such that the beam is focused at position 16, providing at position 16 an image of the filament of the bulb 5 which may for instance be magnified ×3. In general terms, it is not necessary for the beam to be focused at position 16—the beam could be in the form of parallel light at position 16 or diverging. The size of the beam is such that it is wide enough to bathe all the facing surface of the object, but narrow enough for the whole beam to pass in the inlet aperture 29 and pass out the outlet aperture 30 without striking the integrating cavity 17. In effect, the detector 32 will sense the forward-scattered illumination from a roughly collimated beam—the cone outer surface is such that most light striking the object at grazing incidence does not enter the integrating cavity 17.

The signal given by the detector 22 is attenuated by the size of the object, i.e. is responsive to the reduction in flux when the object is in the beam. If it is assumed that virtually no light passes straight through the object, the reduction in flux is the measure of the projected cross-sectional area of the object. As the total forward-scattered light will also depend upon the size of the object, the reduction in flux can be used to normalise the system, and it is found that the measurement of the cross-sectional area is satisfactory, the ratio of forward-scattered, diffused light (detector unit 32) to the cross-sectional area (detector unit 22) being calculated.

Any suitable electronic arrangement can be used for the calculation. FIG. 2 shows schematically the detector unit 32 connected to a micro-processor 41 by way of a pulse amplifier 42, a peak detector 43 (so that the circuit triggers itself), an analogue/digital convertor 44 and means for resetting the circuit for the next measuring cycle. The detector unit 22 is connected to the micro-processor 41 by way of a pulse amplifier/inverter 45, a peak detector 46 and an analogue/digital convertor 47. In the micro-processor 41, the peak signal detected by the detector 32 is divided by the peak reduction in the signal at the detector 22 (the detectors 22, 32 have a straight line response). The clearest possible object available can be used to provide initial calibration. The output from the micro-processor 41 can provide a signal giving a measure of the light transmission or clarity. Alternatively, as shown schematically, it can be used to drive a series of pneumatic solenoid valves 48 connected to a ring of nozzles 49 for blowing the object into one of a number of clarity-sort bins indicated schematically at 50. For instance, in the case of crystalline material, e.g. gemstones such as diamonds or boart, the provision of four clarity-sort bins can significantly reduce hand-sorting though intermediate bins can be provided for those needing re-sorting. If a double-feed detector such as a suitably configured light emitting diode 55 and quadrant detector 51 with a filter 52 is provided in the path of fall of the objects, a further bin can be provided for double feeds, for recycling—in addition, the diode 51 could signal the electronic circuit so that it is ready to accept signals from the detector units 22, 32. A further detector 53 is shown, for detecting the objects as they exit.

Though not shown, the inlet apertures 29 may be closed with removable, slid-in, clear glass, to prevent the occasional object passing into the integrating cavities as a result of incorrect feed. As the glass may become scratched or broken, automatic periodic checks may be made. The apparent brightness of the lamp (5) is reduced by the glass; it decreases still further if the glass is badly scratched and would increase if the glass were broken. The d.c. level detected by the detector unit 22 can therefore be used to monitor the condition of the glass.

Figure 2:
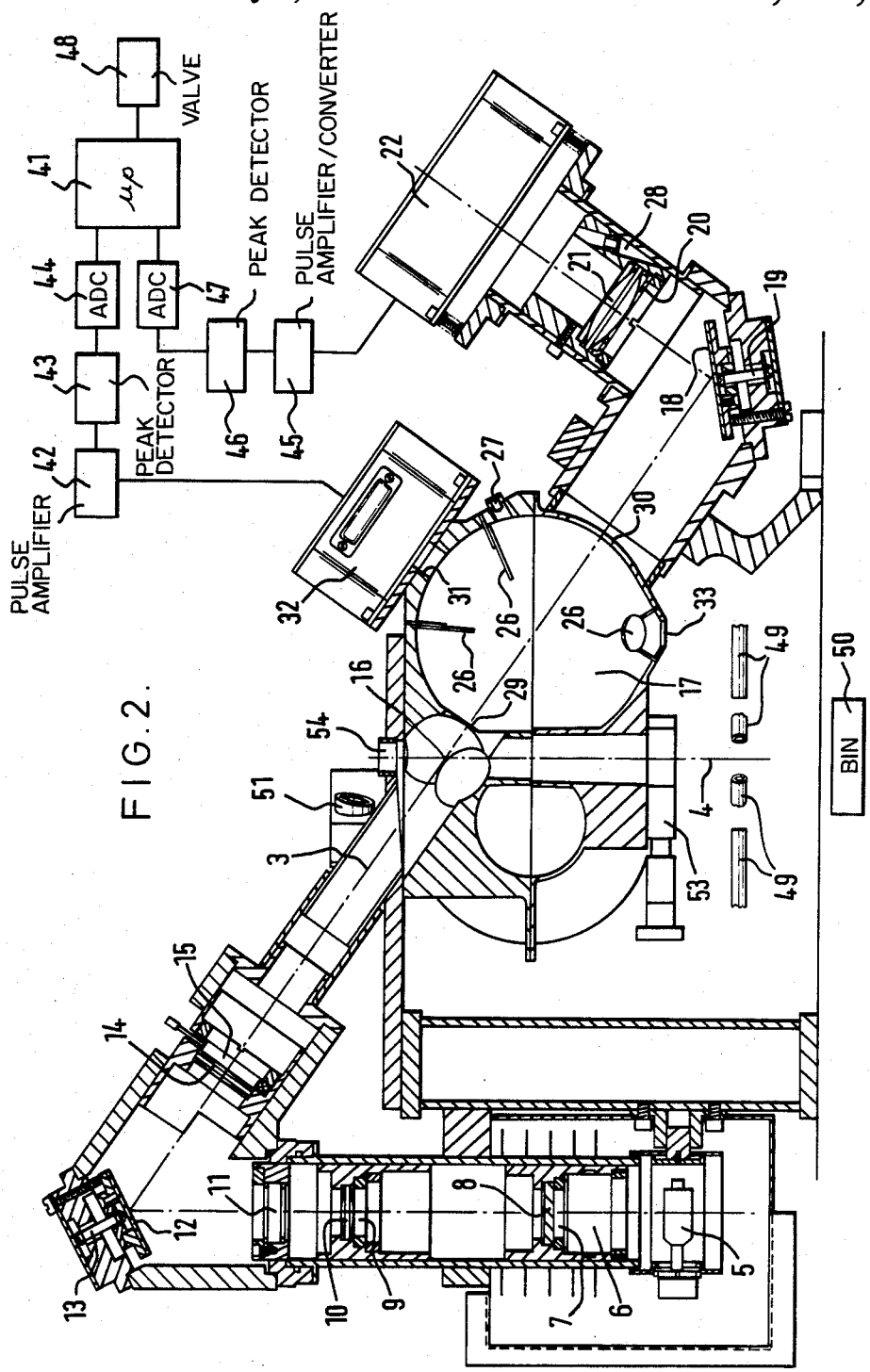
FIG. 2 is a section along the line II—II in FIG. 1.
Figure 3:
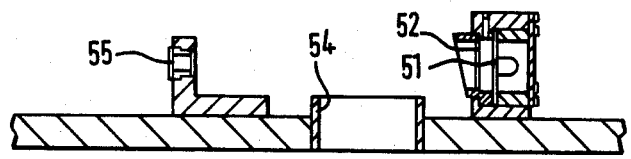
FIG. 3 is a section along the line III—III in FIG. 1.

The arrangement shown in FIG. 2 has an inlet tube 54 whose internal diameter is about 8.5 mm, and it is found that this arrangement can be used for objects of a maximum transverse dimension of 8 mm down to a minimum dimension of about 1 mm.

Although the arrangement described above selects the peak values of the signals from the detector units 22, 32, an alternative is to integrate the signals with respect to time.

Figure 1:
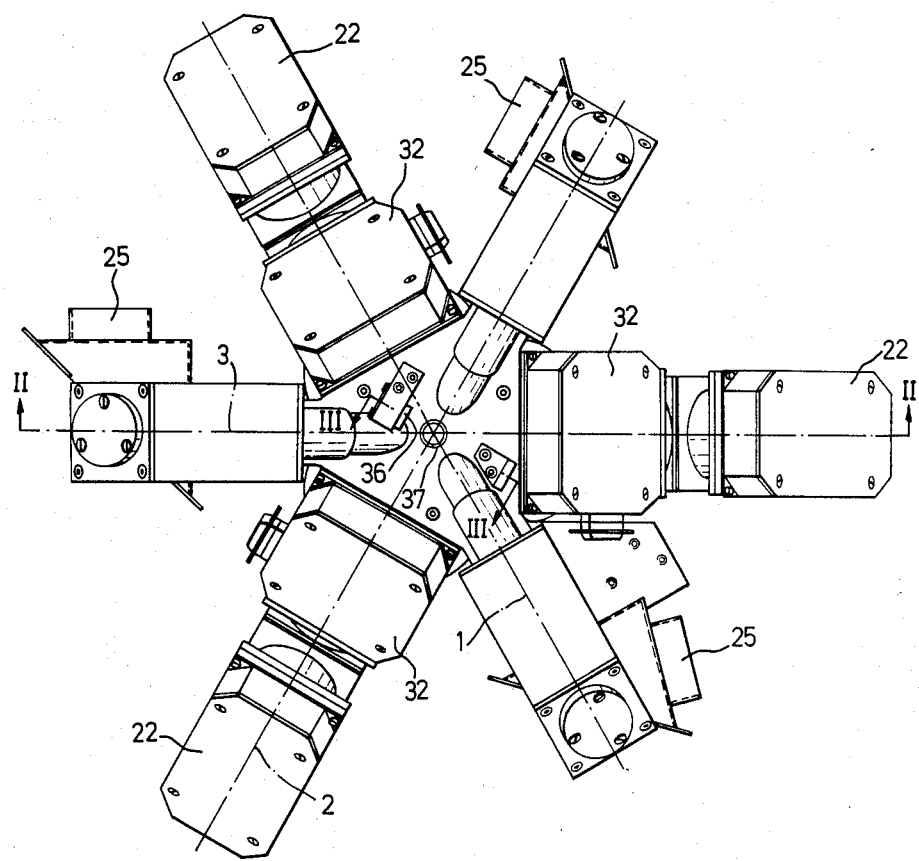
FIG. 1 is a plan view of apparatus for sorting objects according to light transmissivity.

To a large extent, the embodiment would work with just one light path, but the more light paths there are, the better, the most convenient arrangement being the orthogonal arrangement with three light paths, as illustrated in FIG. 1. For the clarity measurement, one can take a straight average (or addition) of the measurements for each path. One problem with more than one path is that there may be cross-talk between the channels. This can be avoided in various ways, for instance by using one wavelength band in each channel or by pulsing the illuminating beams at different times, the pulsing being at sufficiently high frequency for the object to be completely bathed in a uniform flux for each measurement.

The preferred way is to use different wavelength bands, and if only clarity is being examined (and not colour) the near infra-red is preferred for objects such as diamonds, possible band centers being 800, 900 and 1,000 nm (a silicon detector can detect from below 500 nm up to 1,100 nm). With such an arrangement, the first filter 8 can be a Schott RG 695 filter to cut out most visible radiation, the second filter 11 being a suitable band pass filter and the integrating cavity 17 being coated with barium sulphate photometric paint of neutral spectral reflectance—the emitters 26 and 28 can be infra-red diodes. The filter 24 is an infra-red filter and a suitable filter will be provided in the detector unit 32.

Although the visible clarity or visible light transmissivity is being detected, the radiation used need not be visible light provided the transmission of the radiation used gives sufficient indication of visible light transmissivity. Thus, as indicated above, infra-red radiation can be used for suitable objects, as can ultra-violet radiation.

By suitable arrangement, for instance using the pulse system referred to above, it is possible to detect the forward scatter along one path and the side scatter along the other two paths, to obtain information about surface structure and reflectivity. In addition or alternatively, if the beam or beams comprise visible radiation, the integrating cavity or cavities 15 can have means for producing a signal responsive to the colour of visible radiation scattered from the object to enable a colorimetric analysis to be made—the means can be filters or a device for making a spectral analysis. As a further possibility, the path or each path could include another integrating cavity on the nearside of position 16 for detecting back scatter, again to obtain information about surface structure and reflectivity of the object; to achieve this, the arrangement illustrated in FIGS. 1 to 4 would have three further integrating cavities added, providing six orthogonally-arranged integrating cavities.

FIG. 5

Figure 5:
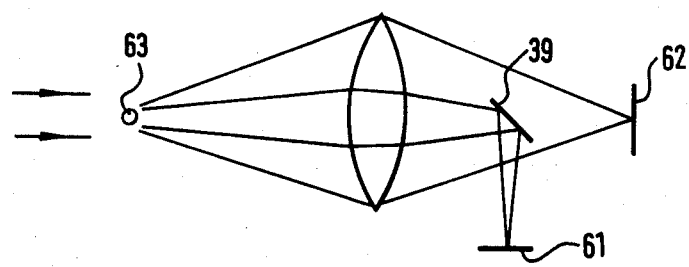
FIG. 5 illustrates part of a different embodiment.

An integrating cavity such as a sphere is a good device for measuring flux independent of the angle of incidence, but other arrangements can be used as said first responsive means and in general anything which measures total flux in a hollow cone. One example is a large annular diode and FIG. 4 gives another example. In FIG. 5, the detector units 61, 62 correspond to the detectors 22, 32 in FIG. 2, the light from the object 63 which is inside the hollow cone reaching the detector 61 by way of a small mirror 64 and the light in the hollow cone reaching the detector 62.

We claim:
1. Apparatus for producing a signal responsive to the transmission of light in object, comprising:
   means for projecting an illuminating beam at each successive object, the beam being wide enough to bathe all the facing surface of the object;

first responsive means for producing a first signal responsive to the total flux of radiation scattered and transmitted through the object in a notional hollow cone optically coaxial with the beam with its apex at the object, the outer surface of the cone having a half-angle substantially less than 90° and the inner surface of the cone having a narrow half-angle;

second responsive means optically coaxial with the beam for producing a second signal responsive to reduction in flux when the object is in the beam; and means receiving said first and second signals for producing a third signal responsive to the transmission of light in each successive object.

2. The apparatus of claim 1, wherein the half-angle of the cone outer surface is 60° or less.

3. The apparatus of claim 1, wherein the half-angle of the cone outer surface is 30° or more.

4. The apparatus of claim 1, wherein the half-angle of the cone outer surface is 30° to 60°.

5. The apparatus of claim 1, wherein the half-angle of the cone inner surface is 10° or less.

6. The apparatus of claim 1, wherein the half-angle of the cone inner surface is 5° or more.

7. The apparatus of claim 1, wherein the half-angle of the cone inner surface is 5° to 10°.

8. The apparatus of claim 1, wherein the first responsive means comprises an integrating cavity having an inlet aperture coaxial with the beam and spaced from a position at which the objects' light transmissivity is determined.

9. The apparatus of claim 8, wherein the integrating cavity has an outlet aperture coaxial with the beam and whose periphery defines said cone inner surface.

10. The apparatus of claim 9, wherein the periphery of the integrating cavity inlet aperture defines said cone outer surface.

11. The apparatus of claim 8, wherein the objects pass outside the integrating cavity.

12. The apparatus of claim 1, wherein on the axis of the beam there is a lens or lens system whose aperture determines the outer surface of said cone, and a beam stop on said axis whose periphery determines the inner surface of said cone, means being provided for permitting said second responsive means to produce a signal responsive to said reduction in flux.

13. The apparatus of claim 12, wherein said second responsive means comprises the beam stop and a sensor, the beam stop being arranged to direct the inner cone of radiation striking the beam stop onto the sensor.

14. The apparatus of claim 1, wherein the objects are moving through the apparatus while their light transmissivity is determined.

15. The apparatus of claim 14, wherein the first and second responsive means are associated with means for selecting the peak value of the signals from the responsive means.

16. The apparatus of claim 14, wherein the first and second responsive means are associated with means for selecting the integral with respect to time of the signals from the responsive means.

17. The apparatus of claim 14, wherein the objects fall through the apparatus while their light transmissivity is determined.

18. The apparatus of claim 1, and comprising a plurality of the projecting means, first responsive means and second responsive means, the projecting means projecting said beams at substantial angles to each other and which intersect at the position at which the objects' light transmissivity is determined.

19. The apparatus of claim 18, wherein there are three projecting means projecting beams mutually at right angles to each other.

20. The apparatus of claim 18, wherein the wavelengths of said beams are different and at least the first responsive means is arranged such that it does not respond substantially to the wavelengths or bands of wavelengths of beams other than the beam projected by the associated projecting means.

21. The apparatus of claim 18, wherein at least one said first responsive means is arranged so that it does not respond substantially to the wavelengths or bands of wavelengths of illuminating beam to which other said first responsive means respond.

22. The apparatus of claim 18, wherein the output of each projecting means is pulsed so that it occurs at a different time from the output of any of the other projecting means, at least the first responsive means being arranged so that they provide an identifiable response at times of the pulsed output by the associated projecting means.

23. The apparatus of claim 18, wherein the first responsive means for one beam is arranged to give an identifiable signal responsive to scattered light from another beam or beams.

24. The apparatus of claim 1, wherein said beam is a beam of infra-red radiation.

25. The apparatus of claim 1, wherein the first and second responsive means respond only to infra-red radiation.

26. The apparatus of claim 1, wherein said beam is a beam of ultra-violet radiation.

27. The apparatus of claim 1, wherein the first and second responsive means respond only to ultra-violet radiation.

28. The apparatus of claim 1, wherein said beam is a beam of visible radiation.

29. The apparatus of claim 1, wherein the first and second responsive means respond only to visible radiation.

30. The apparatus of claim 1, and including means responsive to said third signals for determining the path followed by successive objects after passing through the beam or beams, thereby enabling the objects to be automatically sorted in accordance with their light transmissivity.

31. The apparatus of claim 4, wherein the half-angle of the cone inner surface is 5° to 10°.

32. A method of determining the transmission of light in each of a succession of objects, comprising:

projecting an illuminating beam at each successive object, the beam being wide enough to bathe all the facing surface of the object;

sensing the total flux of radiation scattered and transmitted through the object in a notional hollow cone optically coaxial with the beam with its apex at the object, whose outer surface has a half-angle substantially less than 90° and whose inner surface has a narrow half-angle;

sensing reduction in total flux along the path of the beam when the object is in the beam; and using the detection of the total flux in the hollow cone and the reduction in flux when the object is in the beam to obtain a signal responsive to the transmission of light in the object.

* * * * *